United States Patent [19]

Löhn

[11] Patent Number: 4,944,675
[45] Date of Patent: Jul. 31, 1990

[54] DENTAL SPRAY HANDPIECE

[75] Inventor: Gerd Löhn, Biberach/Rissegg, Fed. Rep. of Germany

[73] Assignee: Kaltenbach & Voigt GmbH & Co., Biberach an det Riss, Fed. Rep. of Germany

[21] Appl. No.: 249,891

[22] Filed: Sep. 27, 1988

[30] Foreign Application Priority Data

Oct. 14, 1987 [DE] Fed. Rep. of Germany ....... 3734831

[51] Int. Cl.$^5$ .............................................. A61C 3/00
[52] U.S. Cl. ........................................ 433/32; 433/84; 433/29; 433/100
[58] Field of Search ....................... 433/80, 82, 84, 85, 433/100, 29, 32

[56] References Cited

U.S. PATENT DOCUMENTS 2,420,338  5/1947  Page ...................... 433/84

FOREIGN PATENT DOCUMENTS 1793042  10/1958  Fed. Rep. of Germany .
1873701  4/1963   Fed. Rep. of Germany .
1466963  5/1969   Fed. Rep. of Germany .
2948577  7/1980   Fed. Rep. of Germany .
2920009  11/1980  Fed. Rep. of Germany .
3208666  9/1983   Fed. Rep. of Germany .
 548768  9/1974   Switzerland .
 658784  12/1986  Switzerland .
 984561  2/1965   United Kingdom ................. 433/85

Primary Examiner—Cary E. Stone
Attorney, Agent, or Firm—Scully, Scott, Murphy & Presser

[57] ABSTRACT

A dental spray handpiece, consisting of a gripping sleeve having a media inlet connection at one end thereof and a media discharge outlet at its other end, the gripping sleeve having media conduits arranged therein which extend from the media inlet connection to the media discharge outlet and discharge media outwardly therefrom. The media conduit has an electrical heating installation associated therewith for heating the medium, as well as a shutoff valve which is adapted to be brought into an open position through finger-actuation.

22 Claims, 2 Drawing Sheets

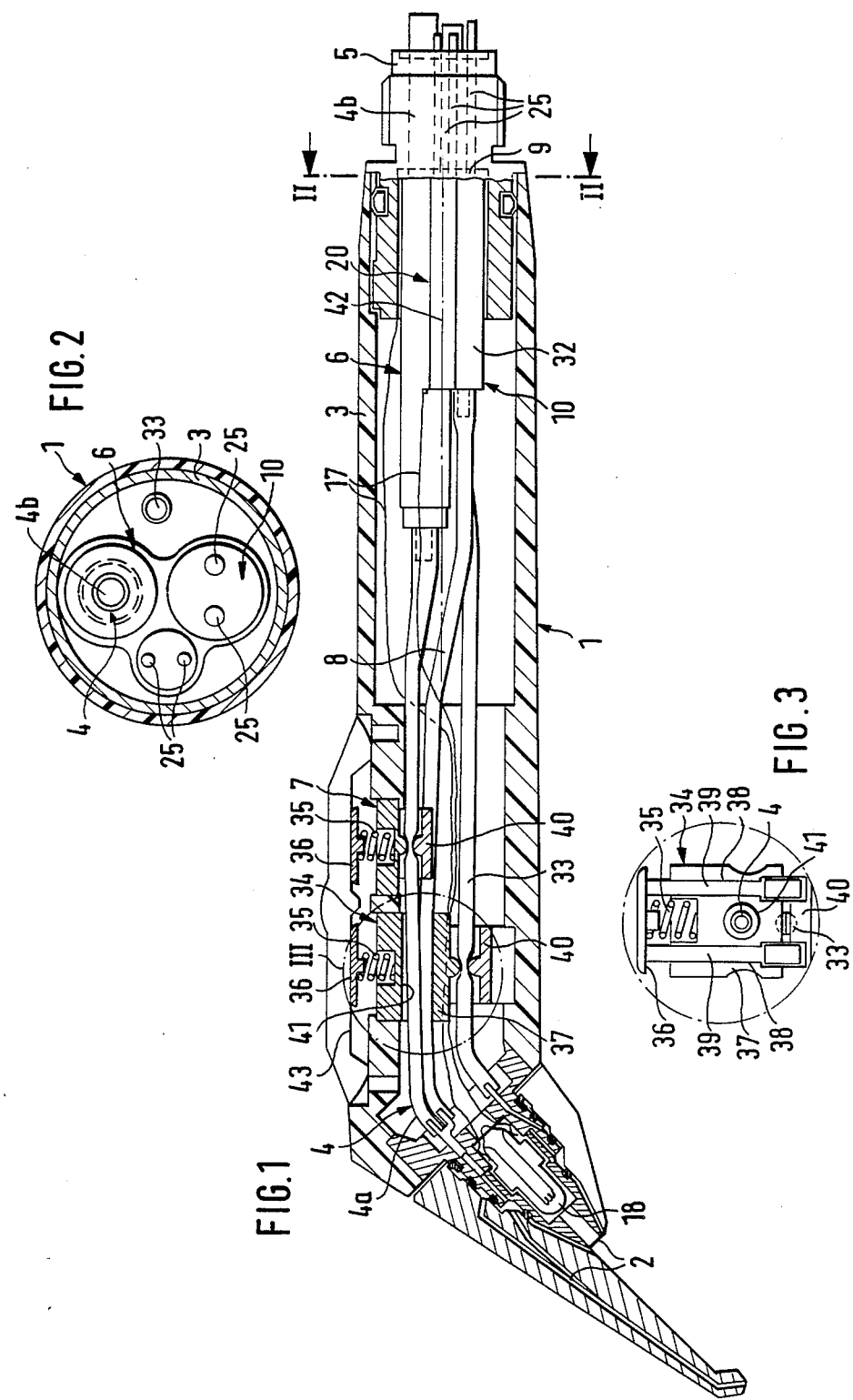

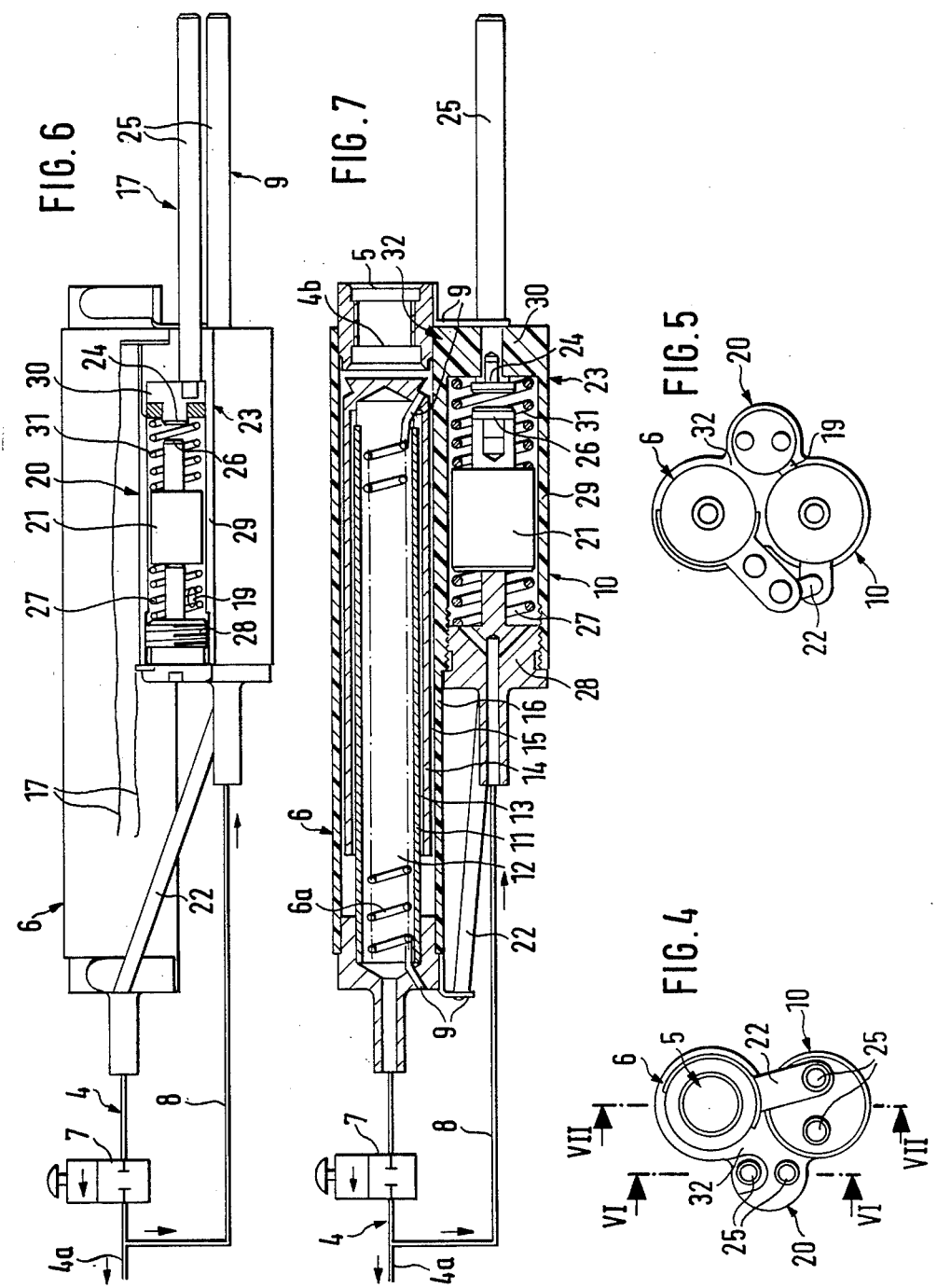

4,944,675

DENTAL SPRAY HANDPIECE

BACKGROUND OF THE INVENTION

1. Field of the Invention

The present invention relates to a dental spray handpiece, consisting of a gripping sleeve having a media inlet connection at one end thereof and a media discharge outlet at its other end, the gripping sleeve having media conduits arranged therein which extend from the media inlet connection to the media discharge outlet and discharge media outwardly therefrom, whereby the media conduit has an electrical heating installation associated therewith for heating the medium, as well as a shutoff valve which is adapted to be brought into an open position through finger-actuation.

For example, the media conduit can convey air or water or spray as a medium.

2. Discussion of the Prior Art

A spray handpiece of that type has become known from the disclosure of German Laid-Open Patent Appln. 29 20 009. In this known spray handpiece, for the actuation of the electrical heating device there is provided an impedance which is dependent upon the temperature of the flowing medium, and an associated signal generating element; in essence, a flow monitor, in conjunction with an electrical circuit. This arrangement is relatively complex and necessitates a considerable amount of space, so as to result in a large constructional volume for the handpiece, as a consequence of which the handling thereof is rendered more difficult.

A further spray handpiece of the above-mentioned type has become known from the disclosure of German Laid-Open Patent Appln. 32 08 666. In this known spray handpiece, a rocker arm or tilt lever mechanism is provided for the regulating of the flow of the media, which quite apparently also serves for the actuation of the electrical heating installation. This rocker-arm mechanism is relatively complicated in construction and also requires a considerable amount of space such that once again, this results in large constructional volume rendering more difficult the handling of the handpiece.

SUMMARY OF THE INVENTION

Accordingly, it is the object of the present invention to provide a dental spray handpiece of the type as is considered hereinabove, wherein a branch line branches off from the media conduit downstream of the shutoff valve, which leads to a pressure-responsive or piezo-electric switch which, upon being subjected to a pressure load, closes a previously interrupted current circuit leading to a heating installation. This handpiece, with a simplified actuation for the heating installation, possesses the smallest possible constructional volume.

The advantages which are achieved by means of the present invention can be essentially ascertained in that the branch line which leads to the piezo-electric switch evidences a relatively small diameter and, furthermore, that the piezo-electric switch which produces a simplified control is a relatively small component, such that the entire control arrangement which is simple in its assembly demands only very little space, as a result of which there is avoided any significant increase in the dimensions of the handpiece; especially the diameter of the handpiece, and thereby its constructional volume; and there is also avoided any increase in difficulties of handling the handpiece.

BRIEF DESCRIPTION OF THE DRAWINGS

Advantageous modifications and features of the invention may now be readily ascertained from the following detailed description as set forth hereinbelow, taken in conjunction with the exemplary embodiments as illustrated in the accompanying drawings; in which:

FIG. 1 illustrates a longitudinal sectional view through the inventive dental spray handpiece;

FIG. 2 illustrates, on an enlarged scale; a transverse sectional view taken along line II—II in FIG. 1;

FIG. 3 illustrates the shutoff valve for the media conduit which is formed by a water line, in the fragmentary detail III encircled in FIG. 1;

FIG. 4 illustrates the media heating installation with a piezo-electric switch for the heating installation and with a piezo-electric switch for an incandescent lamp as a constructional unit which is insertable into the spray handpiece for retrofitting the latter; in a view towards the right end of FIG. 6;

FIG. 5 illustrates the constructional unit of FIG. 4 taken in a view towards the left end of FIG. 6;

FIG. 6 illustrates a sectional view taken along line VI—VI in FIG. 4;

FIG. 7 illustrates a sectional view taken along line VII—VII in FIG. 4.

DETAILED DESCRIPTION OF THE PREFERRED EMBODIMENTS

The illustrated dental spray handpiece 1 consists of a gripping sleeve 3 which possesses a media inlet connection 5 at one end thereof and a media discharge outlet 2 at its other end, at least one media conduit 4 being arranged in the sleeve and leading from the media inlet connection 5 to the media discharge outlet 2 and discharging outwardly therefrom. The media conduit 4 has associated therewith an electrical heating installation 6 which heats the medium flowing through the conduit, as well as a shutoff valve which is adapted to be brought into an open position through finger-actuation. The end of the gripping sleeve 3 which possesses the media discharge outlet 2 is formed in the type of an angled or bent tip. The tip can also be straight in a manner not known shown herein; in essence, it need not extend bent or angled.

Downstream of the shutoff valve 7 a branch line 8 branches off from the media conduit 4, which leads to a pressure-responsive or piezo-electric switch 10 for closing a previously interrupted electrical current circuit 9, and which upon being subjected to pressure leads to actuation of the heating installation 6. Upon actuation of the shutoff valve 7 there is practically concurrently automatically initiated the infeed of media and, with simple means, there is activated the heating installation 6.

The electrical heating installation 6 is arranged in a heating tube 11 streamed through by the medium, which is interconnected with a portion 4a of the media conduit 4 leading to the media discharge outlet 2, which with the formation of an inner annular gap 13 which has its one end in communication with the interior space 12 of the heating tube 11, is encompassed by an intermediate tube 14 which is closed at its other end, which in turn, with the formation of an external annular gap 15 which has one end thereof in communication with the inner annular gap 13, is encompassed by an outer tube 16 which has its other end in communication with the part 4b of the media conduit 4 which is in connection with the media inlet connection 5. Through this arrangement there is achieved that the wall surfaces of the heating tube 11, the intermediate tube 14 and the outer tube 16 are cooled by the inflowing medium; for example, air, and as a result thereof can be constructed extremely thin in order to be able to allow for further savings in space.

The advantageous consequence of the foregoing resides in that the inflowing medium is already warmed up prior to the contact thereof with the heating installation 6, which affords for a savings in electrical current.

The electrical heating installation 6 possesses a heating filament or coil 6a arranged within the heating tube 11. The heating installation 6 is located upstream of the shutoff valve 7.

Within the gripping sleeve 3 there is provided an electrical current supply circuit 17 for the operation of an incandescent lamp or lightbulb 18 which emits light from the media discharge outlet 2, whereby an auxiliary branch line 19 for the medium introduced through the media conduit 4 branches off from the branch line 8 or from the piezo-electric switch 10 of the heating installation 6 branches off the medium conducted through the media conduit 4, wherein auxiliary branch line 19 leads to a previously interrupted current circuit 17 leading to the incandescent lamp 18 closed by the switch 20 at the presence of a pressure load or force. This particular embodiment for the control over the light; as well as the previously mentioned control over the heating, produces a simple control arrangement which operates without the need for any auxiliary actuating elements.

The two pressure-responsive or piezo-electric switches 10 and 20 are each constituted of a cylinder-piston device, whereby piston 21 has the side thereof which is subjected to the pressure from the medium communicating with a conductor 22 of the current circuit 9 or 17, and on its other side includes a switching contact 26 which cooperates with a complementary switching contact 24 of a further conductor 25 of the current circuit which is fixedly located in the cylinder 23.

The piston 21, on the side thereof which is subjected to the pressure of the medium, is connected with the conductor 22 through the intermediary of a coil spring 27 consisting of an electrically-conductive material, as a result of which the coil spring and the switch contact 26 are electrically-conductively interconnected through the piston 21. The coil spring 27 has the end thereof which is distant from the piston 21 electrically-conductively supported against the bottom 28 of the cylinder 23 constituted of an electrically-conductive material, and which is connected with the conductor 22. The jacket or mantle surface 29 of the cylinder 23 and the bottom 30 of the cylinder 23 possessing the counter or complementary switching contact 24 are constituted from an electrically non-conductive material.

Arranged within the cylinder 23, at the side of the piston 21 which possesses the switching contact 26, is a return element 31 acting on the piston, and which is constituted of a helical spring.

The heating installation 6 and the piezo-electric switch 10 which is associated therewith form a single constructional unit with a common housing 32. This type of construction, especially when the housing 32 is an injection-molded component, will produce an easily serviceable embodiment at an inexpensive manufacture cost, inasmuch as the unit can be easily exchanged, and can be easily retrofitted into handpieces without a heating installation 6. This advantage enhances itself, as can be ascertained from FIGS. 4 and 5, when the constructional unit which possesses the common housing 32 also encompasses the pressure-responsive or piezo-electric switch 20 which is associated with the incandescent lamp 18.

The media conduit 4 is an air line. Within the gripping sleeve 3 there is additionally arranged a further media conduit 33 which also leads towards the media discharge outlet 2 and discharges outwardly therefrom, and which is formed by a water line. This water line has a shutoff valve 34 associated therewith which is adapted to be brought into an open position through finger-actuation.

The media conduits 4, 33, or at least a portion thereof, consist of an elastic material, whereby the shutoff valves 7, 34 are constructed as squeeze valves acting on the elastic material.

Further space-saving, inasmuch as only a relatively low constructional height is required for the gripping sleeve 3, as illustrated, is attained when the shutoff valve 7, 34, which are formed as squeeze valves, each respectively possesses a pushbutton 36 which is depressable, against the action of a return spring 35, from a closing position into an open position, whereby the return spring 35 is supported against a bearing block 37 which is fixed to the handpiece. The bearing block is provided with two bores 38 through which there extends two guide rods 39 which are connected with the pressure button 36, and which have their free ends interconnected by means of a squeezing segment 40 clamping, in the closed position, one of the elastic media conduits 7 or 34, or their elastic sections, between themselves and the bearing block 37 under the action of the return spring 35. The savings in space are just as expediently influenced, as illustrated, when the bearing block 37 is provided with a breakthrough 41 for the through-passage of the other media conduit 33 or 4; in the illustrated instance, the media conduit 4 forming the air line.

The shutoff valves 7, 34 are arranged in sequence behind each other along a line extending in parallel with the longitudinal axis 42 of the gripping sleeve 3. The water shutoff valve 34 for the water line 33 is arranged downstream of the shutoff valve 7 for the air line 4.

The savings in space are further enhanced when, in accordance with FIGS. 1 and 3, there is also conducted the branch line 8 through the breakthrough 41 in the bearing block 37. As can be ascertained from FIG. 1, the push-buttons 36 for the shutoff valves 7, 34 are covered by a preferably elastic covering 43.

What is claimed is:

1. Dental spray handpiece comprising a gripping sleeve having a media inlet connection at one end and a media discharge outlet; a media conduit in said sleeve leading from the media inlet connections to the media discharge outlet and discharging outwardly therefrom; electrical heating means for heating media and a shut-off valve which is movable into an open position by finger-actuation, said shut-off valve being associated with said media conduit and a branch line branching off from said media conduit downstream of said shut-off valve, said branch line leading to a pressure-responsive electric switch for closing a previously interrupted electrical current circuit which is connected with said heating means responsive to a pressure force.

2. Spray handpiece as claimed in claim 1, wherein said electrical heating means is in communication with a heating tube in a portion of the media conduit which leads to the media discharge outlet, an annular gap at one end of said heating tube in communication with the inner space of the heating tube being surrounded at the other end by a closed intermediate tube, an outer tube encompassing said intermediate tube so as to form an external annular gap in connection with the inner annular gap, outer tube being in communication at the other end thereof with the portion of the media conduit which is in communication with the media inlet connection.

3. Spray handpiece as claimed in claim 2, wherein electrical heating means includes a heat coil arranged in the heating tube.

4. Spray handpiece as claimed in claim 1, wherein said electrical heating means is arranged upstream of the shutoff valve.

5. Spray handpiece as claimed in claim 1, wherein an electrical current circuit for the operation of an incandescent lamp emitting light from the media discharge outlet is arranged in said gripping sleeve; an auxiliary branch line branching off from said branch line leading to the pressure-responsive electric switch for the heating means for the medium introduced through said media conduit, said auxiliary branch line leading to a further pressure-responsive electric switch which closes the previously interrupted current circuit for the incandescent lamp upon being subjected to a pressure force.

6. Spray handpiece as claimed in claim 5, wherein each said pressure-responsive electric switch in said branch line and said auxiliary branch line comprises a cylinder-piston arrangement, the cylinder having a bottom, and the side of the piston which is subjected to the pressure of medium being connected with an electrical conductor of the current circuit and on the other side having a complementary contact of a further electrical conductor of a switching contact cooperating with the current circuit.

7. Spray handpiece as claimed in claim 6, wherein the piston on the side which is subjected to the pressure of the medium is connected with the electrical conductor through a coil spring constituted of an electrically-conductive material, said coil spring and the switching contact being electrically-conductively interconnected through the piston.

8. Spray handpiece as claimed in claim 7, wherein the coil spring is electrically-conductively supported at the end opposite the piston against the bottom of the cylinder which is connected with the electrical conductor.

9. Spray handpiece as claimed in claim 7, wherein a jacket surface of the cylinder and the bottom of the cylinder having the complementary contact thereon are constituted of an electrically non-conducted material.

10. Spray handpiece as claimed in claim 9, wherein a return element for acting on the piston is provided in the cylinder at the side of the piston possessing the switching contact.

11. Spray handpiece as claimed in claim 10, wherein said return element comprises a helical spring.

12. Spray handpiece as claimed in claim 6, wherein the heating means and the pressure-responsive electric switch associated therewith comprise a constructional unit with a common housing.

13. Spray handpiece as claimed in claim 12, wherein the common housing incorporating said constructional unit encompasses said further pressure-responsive electric switch operatively associated with the incandescent lamp.

14. Spray handpiece as claimed in claim 1, wherein said media conduit comprises an air line.

15. Spray handpiece as claimed in claim 1, wherein a further media conduit is arranged in said gripping sleeve leading to the media discharge outlet and forming an outwardly discharging water line, said further media line having a shutoff valve therein which is movable into an open position through finger-actuation.

16. Spray handpiece as claimed in claim 15, wherein at least portions of said media conduits are constituted of an elastic material, said shutoff valves being squeeze valves adapted to compress the elastic material.

17. Spray handpiece as claimed in claim 16, wherein the shutoff valves comprising the squeeze valves each possess a depressable pushbutton which is operable against of the action of a return spring from a closed position into an open position, said return spring being supported against a bearing block positioned in the handpiece, said bearing block including two bores through which there extend two guide rods which are connected with the pushbutton and which at their free ends are interconnected by a squeezing element clampingly operating on the elastic media conduit or the elastic portion between themselves and the bearing block responsive to the action of the return spring.

18. Spray handpiece as claimed in claim 17, wherein said bearing block includes a breakthrough for the through-passage of said further media conduit.

19. Spray handpiece as claimed in claim 18, wherein said branch line is conducted through the breakthrough in said bearing block.

20. Spray handpiece as claimed in claim 17, wherein the pushbuttons of said shutoff valves are covered by an elastic covering.

21. Spray handpiece as claimed in claim 15, wherein said shutoff valves are arranged in a linear sequence in parallel with the longitudinal axis of the gripping sleeve.

22. Spray handpiece as claimed in claim 15, wherein the shutoff valve for the water line is arranged downstream of the shutoff valve for an air line.

* * * * *